United States Patent [19]

Kolobow

[11] Patent Number: 5,711,296
[45] Date of Patent: Jan. 27, 1998

[54] CONTINUOUS POSITIVE AIRWAY PRESSURE SYSTEM

[75] Inventor: Theodor Kolobow, Rockville, Md.

[73] Assignee: The United States of America as represented by the Department of Health and Human Services, Washington, D.C.

[21] Appl. No.: 231,718

[22] Filed: Apr. 22, 1994

Related U.S. Application Data

[63] Continuation-in-part of Ser. No. 85,948, Jul. 6, 1993, Pat. No. 5,429,127, which is a continuation-in-part of Ser. No. 878,784, May 6, 1992, Pat. No. 5,305,740, which is a continuation-in-part of Ser. No. 758,824, Sep. 12, 1991, abandoned.

[51] Int. Cl.$^6$ .................................................. A61M 16/08
[52] U.S. Cl. ........................ 128/205.13; 128/205.14; 128/205.16; 128/204.28
[58] Field of Search .................. 128/205.43, 205.14, 128/205.15, 205.16, 207.15, 207.14, 204.28

[56] References Cited

U.S. PATENT DOCUMENTS

| | | | |
|---|---|---|---|
| 514,448 | 2/1894 | Desant | 128/205.18 |
| 896,824 | 8/1908 | Habberley | 128/205.18 |
| 1,120,673 | 12/1914 | Bayer | 128/205.18 |
| 1,213,302 | 1/1917 | Tullar | 128/205.18 |
| 2,217,575 | 10/1940 | Von Hoff | 128/205.14 |
| 3,402,711 | 9/1968 | Emerson | 128/204.28 |
| 3,467,092 | 9/1969 | Bird et al. | 128/205.15 |
| 3,837,337 | 9/1974 | LaViolette | 128/205.12 |
| 3,916,888 | 11/1975 | Buck et al. | 128/204.21 |
| 3,923,053 | 12/1975 | Jansson | 28/205.13 |
| 4,176,663 | 12/1979 | Hewlett | 128/205.16 |
| 4,270,530 | 6/1981 | Baum et al. | 128/207.15 |
| 4,299,216 | 11/1981 | Bernard et al. | 128/205.12 |
| 4,340,044 | 7/1982 | Levy et al. | 128/204.21 |
| 4,630,606 | 12/1986 | Weerda et al. | 128/207.14 |
| 5,019,040 | 5/1991 | Itaoka et al. | 604/95 |
| 5,048,517 | 9/1991 | Pasternack | 128/205.28 |
| 5,186,167 | 2/1993 | Kolobow | 128/207.14 |

FOREIGN PATENT DOCUMENTS

| | | | |
|---|---|---|---|
| 232864 | 8/1987 | European Pat. Off. | |
| 0559977 | 9/1993 | European Pat. Off. | |
| 982325 | 6/1951 | France | 128/204.28 |
| 1160627 | 7/1958 | France | |
| 1487768 | 7/1967 | France | 128/205.15 |
| 2033759 | 5/1980 | United Kingdom | |
| 9304725 | 3/1993 | WIPO | |
| 9501813 | 1/1995 | WIPO | |

OTHER PUBLICATIONS

*Silastic Endotracheal tube*, Dow Corning, Don Miller, "Tracheal Stenosis Following Proboy Cuffed Intubation: Causes & Prevention Annals of Surgery", vol. 171, No. 2, Feb. 1970.

Mushin, William W., "Automatic Ventilation of the Lungs" Blackwell Scientific Publications, Oxford London Edinburgh Melbourne 16610, 1980 pp. 536–543.

*Primary Examiner*—V. Millin
*Assistant Examiner*—William J. Deane, Jr.
*Attorney, Agent, or Firm*—Lowe, Price, Leblanc & Becker

[57] ABSTRACT

A passive continuous positive airway intratracheal pulmonary ventilation system which includes an inspiration limb and an expiration limb which are pressure balanced by inflatable bags. An intratracheal pulmonary ventilation system is provided which includes a catheter having a tip which is positioned through a low resistance endotracheal tube at or near a patient's carina. A constant source of an oxygen-containing gas flows through the catheter. The catheter has a tip which deflects and reverses the flow direction of the oxygen-containing gas.

14 Claims, 9 Drawing Sheets

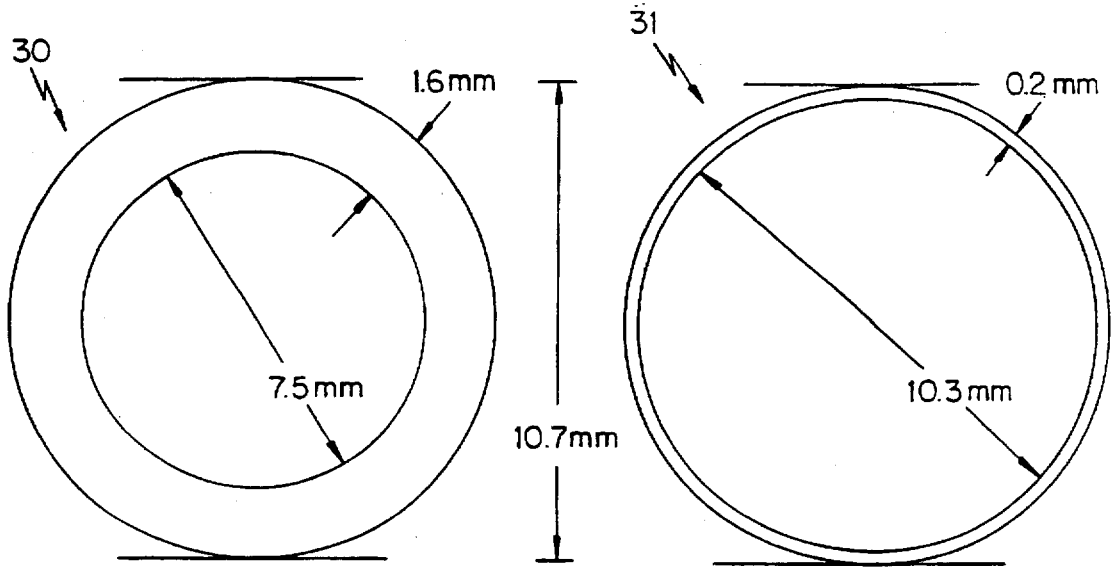
FIGURE 6A
PRIOR ART
FIGURE 6B
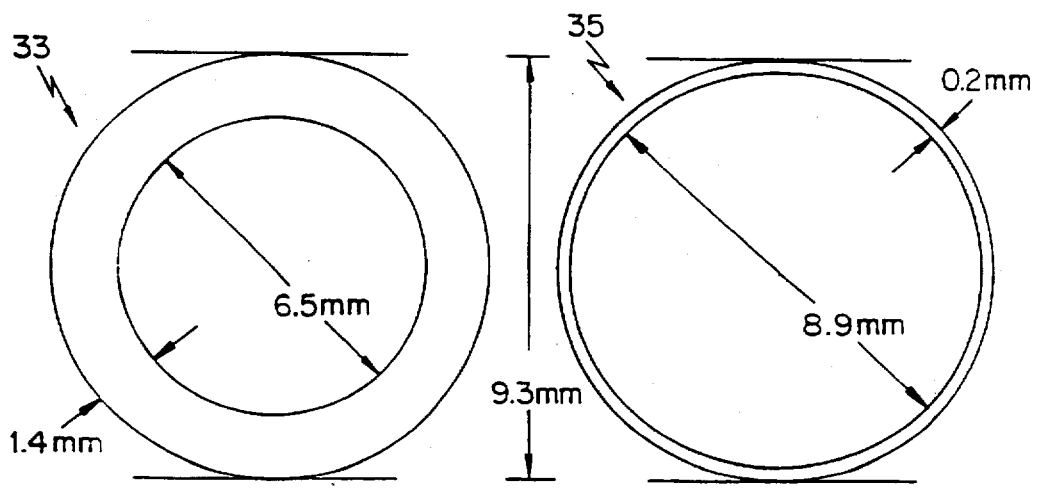
FIGURE 7A
PRIOR ART
FIGURE 7B

CONTINUOUS POSITIVE AIRWAY PRESSURE SYSTEM

RELATED APPLICATIONS

This application is a continuation-in-part of U.S. patent application Ser. No. 08/085,948, filed Jul. 6, 1993, now U.S. Pat. No. 5,429,127, which is a continuation-in-part of U.S. patent application Ser. No. 07/878,784, filed May 6, 1992 now U.S. Pat. No. 5,305,740 which is a continuation-in-part of U.S. patent application Ser. No. 07/758,824, filed Sep. 12, 1991, now abandoned the complete disclosures of which are expressly incorporated herein by reference.

Technical Field

The present invention relates to intratracheal ventilation and intratracheal pulmonary ventilation methods and apparatus. More particularly, the present invention relates to methods and apparatus for sustaining spontaneous breathing in patients with severe respiratory failure.

BACKGROUND ART

Continuous Positive Airway Pressure (CPAP) is widely used in patient treatment for mild respiratory failure in newborns, children and adults. CPAP refers to a method in which the patient initiates all breathing. The constant back pressure in CPAP provides the force to re-expand some diseased parts of the lungs and hence improves oxygenation and carbon dioxide removal. CPAP systems which are currently in use suffer some major drawbacks. In particular, in intubated patients, currently available endotracheal tubes (ETT's) have a substantial airway resistance as compared to the resistance of the upper airways. This resistance can lead to an increase in the work of breathing, and fatigue. Too often, a patient receiving CPAP treatment is eventually placed on assisted mechanical ventilation of one type or another. This increases the risk of barotrauma and is associated with a significant increase in morbidity and mortality.

The peak inspiratory and expiratory air flows in current CPAP systems is severely limited. This contributes to patient discomfort, and often times becomes the motivation for switching a patient to assisted mechanical ventilation.

The field of Continuous Positive Airway Pressure (CPAP) has been dormant for years. Nevertheless, many patients managed on a mechanical pulmonary ventilator could potentially be better served by a CPAP, The present invention greatly enhances the utility of CPAP as currently applied and widens its use to the treatment of more sever forms of acute respiratory failure.

DISCLOSURE OF THE INVENTION

It is accordingly one object of the present invention to provide a passive continuous positive airway pressure (CPAP) ventilation system.

Another object of the present invention is to provide a passive continuous positive airway pressure ventilation system (CPAP) which is combined together with an intratracheal pulmonary ventilation (ITPV) system A further object of the present invention is to provide a pulmonary ventilation system which has exceptionally low extrinsic resistance to air flow and greatly reduces dead space ventilation.

It is a further object of the present invention to provide a method of passive continuous positive airway pressure (CPAP) ventilation.

A still further object of the present invention is to provide a method of passive continuous positive airway pressure ventilation system (CPAP) which is combined together with a method of intratracheal pulmonary ventilation (ITPV).

According to these and further objects of the present invention which will become apparent as the description thereof proceeds, the present invention provides a passive continuous positive airway intratracheal pulmonary ventilation apparatus which includes:

an inspiration limb which includes a first inflatable bag, means for applying a force to the first inflatable bag, and a first one-way valve for providing an inspiration flow of an oxygen-containing gas;

an expiration limb which includes a second inflatable bag, means for applying a force to the second inflatable bag, and a second one-way valve for providing an expiration flow of the oxygen-containing gas; and an endotracheal tube connected between the inspiration limb and the expiration limb for directing the inspiration flow of the oxygen-containing gas to a patient and for directing the expiration flow of the oxygen-containing gas from the patient.

The present invention further provides for a method of providing passive Continuous positive airway intratracheal pulmonary ventilation to a patient which involves:

inserting a endotracheal tube into a patient's trachea;

connecting the endotracheal tube to a continuous source of an oxygen-containing gas which is supplied at a constant pressure during inspiration and expiration thereof by the patient;

inserting a catheter through the endotracheal tube and positioning a tip of the catheter near the patient's carina; and supplying a constant flow of an oxygen-containing gas through the catheter.

BRIEF DESCRIPTION OF DRAWING

The present invention will be described with reference to that attached drawings which are given by way of non-limiting examples only, in which:

FIG. 6A shows an end view of a prior art endotracheal tube.

FIG. 6B shows an end view of an endotracheal tube according to the present invention.

FIG. 7A shows an end view of another prior art endotracheal tube.

FIG. 7B shows an end view of a smaller size ultra-thin walled wire reinforced endotracheal tube of the present invention.

Best Mode for Carrying out the Invention

The present invention is directed to an integrated, highly efficient, patient friendly CPAP system which is combined with an Intratracheal Pulmonary Ventilation (ITPV) system. The system of the present invention provides an exceptionally low extrinsic resistance to air flow through the use of low resistance endotracheal tubes (ETT's) and greatly reduces dead space ventilation through the use of ITPV using a Reverse Thrust Catheter (RTC). The external resistance to air/oxygen flow in the system substantially equals the resistance associated with normal upper airways in healthy adults, children and newborns.

The system of the present invention allows a patient to inhale and exhale comfortably even at high peak inspiratory and expiratory flows and high respiratory rates. Thus, the patient does not become exhausted nor experience a feeling of shortness of breath. The system incorporates a balanced balloon (bag) system which supplies CPAP in a manner that allows for both highest peak inspiratory flows and expiratory flows. The system as devised further has a minimal waste of gas flow. Spontaneous tidal volumes generated by the patient can be as low as 2 to 3 ml/kg, albeit higher respiratory rates greatly reduce the work of breathing. Use of the present system allows for CPAP pressures of up to about 10 cm.$H_2O$ in most patients.

The system of the present invention will permit a large fraction of the current patient population supported by assisted mechanical ventilation to switch to CPAP or a combination of CPAP and ITPV. As a result, barotrauma associated with high peak inspiratory pressure mechanical ventilation can be prevented. In addition, the perception of controlling one's own breathing, comfortably, is an important emotional factor which increases patient cooperation, and can reduce the need for sedatives/paralysis. Since pulmonary ventilation can be sustained through spontaneous breathing, the present system provides the safest mode of ventilation.

Figures 1, 2:
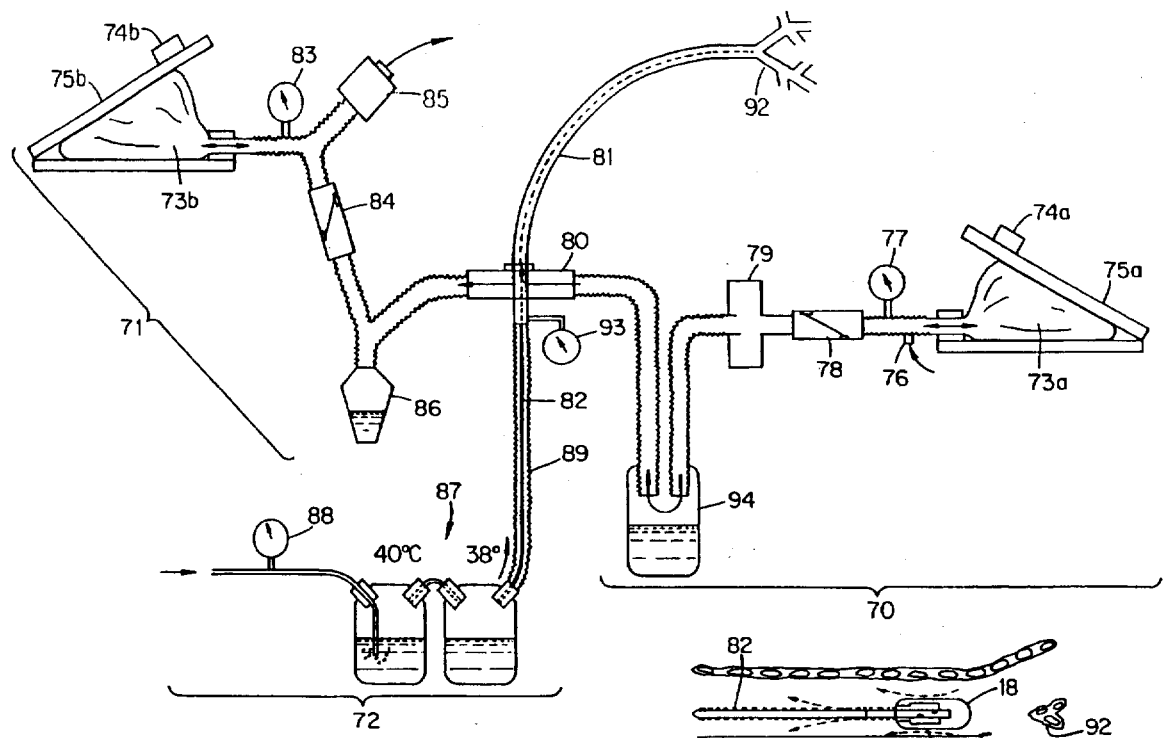
FIG. 1 is a schematic representation of a CPAP system according to one embodiment of the present invention.
FIG. 2 is a schematic diagram illustrating the positioning of a catheter tip and a pressure sensor according to one embodiment of the present invention.

FIG. 1 is a schematic representation of a CPAP system according to one embodiment of the present invention. The system depicted in FIG. 1 includes an inspiratory limb 70, an expiratory limb 71, (which together define a CPAP system) and an ITPV section 72.

Each of the inspiratory and expiratory limbs includes a means for balancing and maintaining gas pressure within the system. These means for balancing and maintaining gas pressure include inflatable bags 73a and 73b. Suitable inflatable bags can include anesthesia balloons, bellows, or the like. The means for balancing and maintaining gas pressure also include a means to apply a constant force to the inflatable bags 73a and 73b. According to a preferred embodiment which is depicted in FIG. 1, weights 74a and 74b are used as the means to apply a constant force on the inflatable bags 73a and 73b.

In order to support the weights 74a and 74b in position, support frames 75a and 75b are provided. The support frames 75a and 75b shown in FIG. 1 are hinged plates, between which the inflatable bags 73a and 73b are positioned. The weights 74a and 74b are positioned over the inflatable bags 73a and 73b on the top of the hinged plates as shown.

In alternative embodiments, the support frames 75a and 75b can include a upper plate which is guided to freely move in the vertical direction, above the inflatable bags 73a and 73b. In further embodiments, the weights 74a and 74b could be replaced with constant force springs. Other, more complex means could be used to apply a constant force to the inflatable bags 73a and 73b, such as sensor controlled pneumatic or hydraulic presses. However, simplicity of the system would be sacrificed.

The inflatable bags 73a and 73b and the means to apply a constant force thereto ensure that a constant source of CPAP is available throughout the system.

Air and/or oxygen is supplied to the system through the inspiratory limb 70. For this purpose, a gas supply port 76 is provided in the inspiration limb 70. A pressure monitor/sensor or gage 77 is provided in the inspiratory limb 70 to monitor the pressure in the inspiratory limb 70. A one-way valve 78 is provided in the inspiratory limb 70 downstream of the gas supply port 76 and the pressure monitor/sensor or gage 77. This one-way valve 78 controls the flow direction of fresh air and/or oxygen during breathing.

FIG. 1 depicts a pneumotachograph 79 which is optionally provided for monitoring changes in the internal pressure of the system during use. During the course of the present invention, the pneumotachograph 79 was used for research purposes. The inspiration limb 70 also includes a humidifier 94 which is connected between the one-way valve 78 and fitting 80.

The inspiratory limb 70 and expiratory limb 71 are connected to either sides of fitting 80. Fitting 80 is also connected to endotracheal tube 81 and ITPV catheter 82, as discussed below.

The expiratory limb 71 also includes a pressure monitor/sensor and gage 83 and a one-way valve 84. In addition, the expiratory limb 71 includes a Positive End Expiratory Pressure (PEEP) regulator 85 of conventional design. The PEEP regulator 85 is essentially a throttle valve which is adjusted to maintain a desired pressure in the inspiration limb 70 and expiration limb 71. In this regard, the PEEP regulator allows for a constant expiratory leak that occurs both during inspiration and expiration. As discussed below, and otherwise apparent, the gas pressure in the system is controlled by adjusting the PEEP regulator 85, the air and/or oxygen feed through gas supply valve 76, and the mass of the weights 74a and 74b positioned above the inflatable bags 73a and 73b.

The expiratory limb 71 also includes an expiratory water trap 86.

The ITPV section 72 includes a two-stage humidifier system 87 which is connected to a source of air and/or oxygen (not shown). A pressure monitor/sensor or gage 88 is provided between the two-stage humidifier system 87 and the source of air and/or oxygen and is used to monitor the supply pressure of the air and/or oxygen gas. The air and/or oxygen gas is heated or cooled as desired by the two-stage humidifier 87. For this purpose, the humidifier system includes appropriate heater and cooling means which can be of conventional design.

An insulated ITPV catheter 82 connects the two-stage humidifier system 87 to fitting 80. The preferred ITPV catheter 82 used according to the present invention is disclosed in U.S. Pat. No. 5,186,167, the complete disclosure of which is expressly incorporated herein by reference. This catheter has a reverse thrust tip (FIG. 2) which greatly reduces back pressure which can cause over inflation of the lungs. The ITPV catheter is provided with an insulating sheath or jacket 89 between the two-stage humidifier system 87 and fitting 80. On the opposite side of fitting 80 the ITPV catheter enters ultra-low resistance endotracheal tube 81 is discussed in detail below.

FIG. 2 is a schematic diagram illustrating the manner in which the tip 90 of the ITPV catheter 82 and a carinal pressure sensor 91 are positioned according to one embodiment of the present invention. As depicted in FIG. 2 the ITPV catheter 82 is passed through the endotracheal tube 81 so that the tip 90 of the catheter 81 is positioned at or near the level of the patient's carina 92. In order to prevent kinking of the catheter, the catheter 81 may be inserted and positioned with the aid of a guide wire (not shown). A carinal pressure monitoring catheter 91 is also passed through the endotracheal tube 81. The carinal pressure monitoring catheter 91 extends just beyond the tip 90 of the ITPV catheter 82 as depicted in FIG. 2 and is connected to a carinal airway pressure monitor or gage 93.

In operation, weights 74a and 74b, inflatable bags 73a and 73b, and support frames 75a and 75b are matched so as to ensure an identical compliance between the inspiratory and expiratory limbs. The air and/or oxygen flow into gas supply port 76 is set at a level sufficient to keep the inflatable bags 73a and 73b in the inspiratory and expiratory limbs partially inflated. The PEEP regulator 85 is simultaneously adjusted to maintain a desired pressure in the system.

The Positive End Expiratory Pressure (PEEP) can be adjusted by changing the force, e.g. weight, applied to the inflatable bags 73a and 73b, and adjusting the PEEP regulator 85. For a higher PEEP, the mass of weights 74a and 74b is increased and the PEEP regulator 85 is adjusted to maintain a higher pressure.

As discussed above, the ITPV catheter 82 is passed through the endotracheal tube 81 so that the tip 90 of the catheter 82 is positioned at or near the level of the patient's carina 92. In order to prevent kinking of the catheter, the catheter 82 may be inserted and positioned with the aid of a guide wire (not shown). A carinal pressure monitoring catheter 91 is also passed through the endotracheal tube 81. The carinal pressure monitoring catheter 91 extends just beyond the tip 90 of the ITPV catheter 82 as depicted in FIG. 2.

During spontaneous breathing, air and/or oxygen from the inspiratory limb 70 enters the lungs, and exits through the expiratory limb 71. One-way valves 78 and 84 provide for unidirectional flow.

The ITPV section greatly reduces dead space ventilation by delivering a constant fresh supply of air and/or oxygen directly at the level of the carina 92. Depending on the degree of lung impairment and respiratory rates, potentially all fresh gas can be provided by either the ITPV system or by the combined ITPV and CPAP system. It is noted that the system can be easily converted to a fully mechanical pulmonary ventilator by including a timed on/off valve in the endotracheal tube 81. When such a valve is provided and closed, the air and/or oxygen supplied to the ITPV catheter would inflate the patient's lungs. Opening the valve would then allow for expiration.

The low resistance endotracheal tube used in the CPAP system of the present invention will be described hereafter. First, with reference now to FIG. 3, a schematic representation of an apparatus adapted for making ultra-thin walled wire reinforced endotracheal tube is illustrated. The apparatus is generally designated by the reference numeral 10 and is seen to include a cylindrical mandrel 1 having a release agent coating on the surface 2 thereof. The release agent 2 is designed to facilitate removal of the ultra-thin walled wire reinforced endotracheal tubing from the cylindrical mandrel 1. The release agent may be any agent known in the art such as Teflon ®. The cylindrical mandrel may be made of any material having sufficient strength to provide support for the tubing, preferably a steel rod.

The cylindrical mandrel is connected to a lathe means 3 which includes drive means therewith to rotate the mandrel at a predetermined speed. Of course, any known means capable of rotating a cylindrical mandrel may be utilized in substitution for the lathe 3.

The apparatus for making the ultra-thin walled wire reinforced endotracheal tubing also includes a polymer source means 5 which supplies a dissolvable polymer such as polyurethane Lycra® under pressure to a metering pump 9 via the line 7. The polymer source means 5 may be a closed container including a source of inert gas to provide the pressure to supply the dissolved polymer to the metering pumping 9. Preferably, the source of the pressure is a dry nitrogen or other inert gas.

The metering pump 9 includes a nozzle 11 made out of a flexible tubing such as Teflon ®. The tubing 11 should have sufficient flexibility and thickness to follow the contours of the cylindrical mandrel 1 and float on the polymer layer as it emerges from the nozzle. The flexibility of the tubing 1 may be enhanced by the addition of a spring material surrounding the tubing. The metering pump 9 may be a gear fluid pump designed to meter a solution of polymer onto the mandrel.

The polymer source means 5 and metering pump means 9 also include a cross feed means which permits the source means 5, metering means 9 and nozzle 11 to traverse the length of the mandrel 1. As illustrated by the reference numeral 21 in FIG. 3, the source means 5, metering pump 9 and nozzle 11 are displaced along the longitudinal axis of the cylindrical mandrel 1. The longitudinal movement of the nozzle 11 permits that polymer to be continuous applied to the mandrel 1 over a preselected pattern. When fabricating a two-stage endotracheal tube according to the present invention, the mandrel 1 will be provided with an appropriate contour. In such a case, suitable mechanical positioning means can be used to move tubing 11 along the contour of the mandrel 1.

A control means 13 is provided that regulates the deposition of the polymer on the mandrel 1. The control means 13 is connected to the polymer source means 5 via the line 15, the metering pump 9 via the line 17 and the lathe 3 via the line 19. By controlling the rotation of the mandrel 1 via the lathe 3 and the amount of polymer deposited on the mandrel 1, the thickness of polymer applied to the mandrel or wall thickness of the ultra-thin walled and wire reinforced endotracheal tubing may be controlled and varied. The control means 13 also provides control over longitudinal traversing of the nozzle 11 and associated components and the cylindrical mandrel 1. It should be understood that, although the nozzle 11, metering pump 9 and polymer source means 5 are depicted as longitudinally traversing the length of the cylindrical mandrel 1, in another embodiment, the polymer source means 5 may be stationery with the metering pump 9 and nozzle 11 traversing the length of the mandrel 1. It should be understood that the mechanism for providing the longitudinal traversing movement of either the metering pump 9 and nozzle 11 or these components with the polymer source means 5 are well recognized in the prior art. For example, these components may be longitudinally traversed using a drive means and rack and pinion gearing. Likewise, a similar known mechanism can be incorporated to move nozzle 11 to follow the contour of the mandrel 1 if necessary.

The apparatus 10 also includes a heating means 23 which supplies heat such as hot air to the mandrel 1 to dry the polymer solution after deposition on the mandrel.

The heating means may a strip heater or other known heating means. The heating means 23 may also include individually adjustable baffles 25 which facilitate directing the hot air toward the mandrel 1. The adjustable feature of the baffles 25 permit varying the amount of drying air along the length of the mandrel 1. For example, when producing a tapered endotracheal tube, certain areas of the tube having increased wall thickness require a higher heat input for drying purposes. In this situation, the individually adjustable baffles are arranged to direct more hot air to the portion of the cylindrical mandrel having the endotracheal tube with increased wall thickness.

Figure 3:
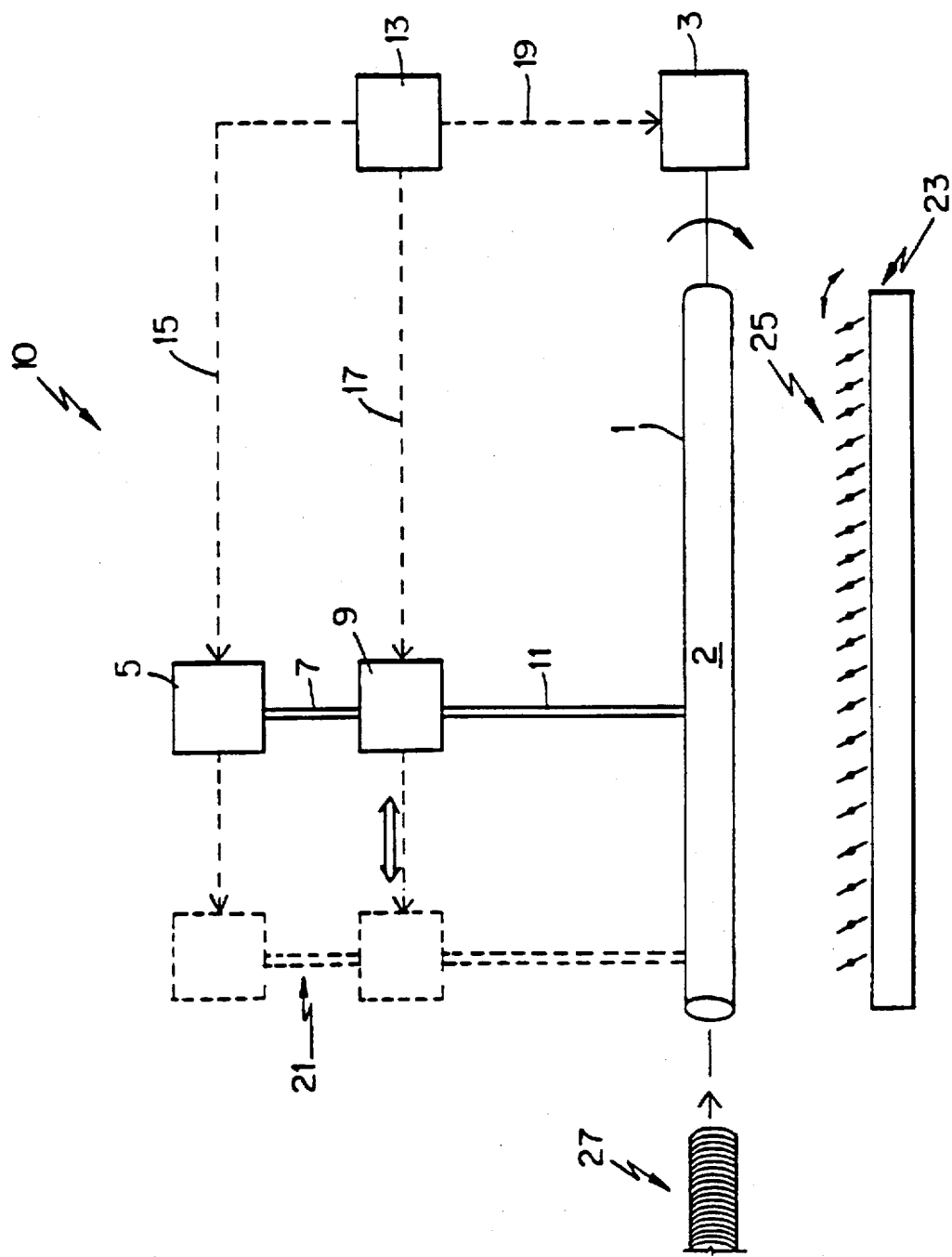
FIG. 3 shows a schematic representation of one embodiment of the apparatus utilized for making the ultra-thin walled wire reinforced endotracheal tubing.
Figure 11:
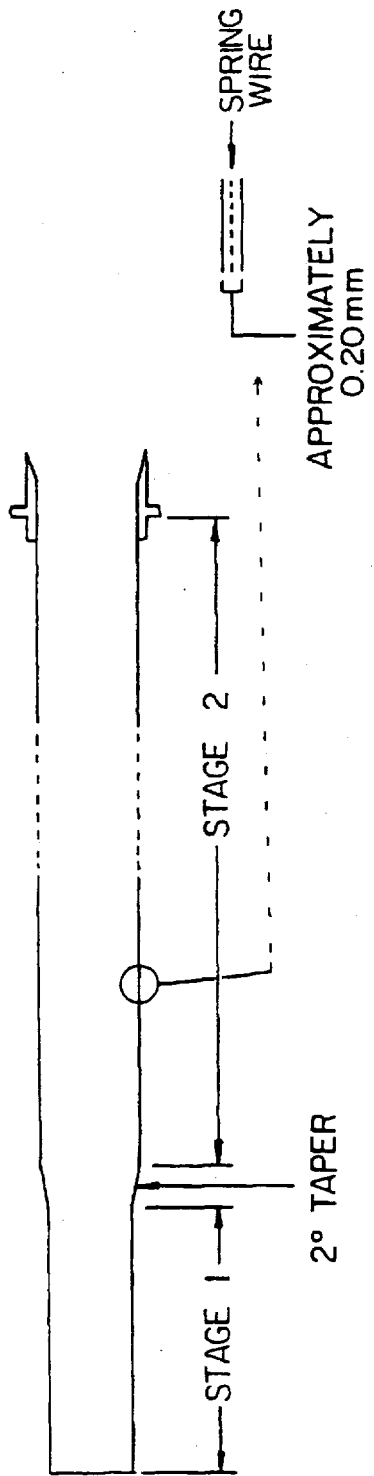
FIG. 11 is a schematic cross sectional side view of an ultra-thin two-stage endotracheal tube according to the present invention.

FIG. 3 also depicts a coil spring 27 which is designed to be inserted over the Teflon® coated cylindrical mandrel 1. The spring 27 may be manually inserted over the rod or, alternatively, by known mechanical means. As an alternative embodiment, the spring material may be in the form of an unwound wire or flat material and be wound around the cylindrical mandrel in a known fashion. As will be described hereinafter, the spring 27 may be applied to the mandrel 1 after or during the deposition of the polymeric material. The method of making the ultra-thin walled wire reinforced endotracheal tubes according to the present invention will now be described. First, a mandrel is machined from a suitable material such as steel to the exact internal dimensions of the desired endotracheal tube. According to one embodiment, the mandrel can be of the same dimension throughout as in conventional endotracheal tubes (ultra-thin ETT, UT ETT). In another embodiment the mandrel can be provided with a short section with a smaller diameter (to rest within the trachea), and gradually tapering at a 2° angle to a larger diameter for the oropharyngeal section (ultra-thin two-staged ETT, UTTS ETT) (FIG. 11). Following this, the mandrel is placed in a rotating lathe and a solution of polyurethane (Lycra®) in a compatible solvent, e.g. dimethylacetamide (DMA) is metered onto the rotating mandrel. A typical concentration of polymeric material would range between 10–30 weight percent polymer in the solvent, with about 15 weight percent polymer being ideal.

This range is only exemplary and greater or lesser concentrations of polymeric material may be utilized depending on the particular polymer being employed. The dissolved polymer is supplied to a metering pump under pressure such as dry nitrogen. The metering pump, such as a fluid gear pump, meters the dissolved polymer unto the rotating surface of the mandrel while the nozzle traverses the length of the cylindrical mandrel. The deposited polymer is permitted to air dry, or alternatively, dry by application of a source of heat such as a strip heater or the like. This sequence may be repeated if an increased thickness of polymeric material is desired on the surface of the cylindrical mandrel.

By choosing a particular rate of deposition of polymeric material, the solvent evaporation rate can be optimized such that one layer of polymer can be deposited onto the previously deposited and dried layer to build up thickness. In a further embodiment, successive deposition of several layers of polymeric solution may be performed while traversing the cylindrical mandrel on a single run. In this embodiment, a plurality of nozzles may be utilized which are spaced apart from each other such that following nozzles are depositing polymeric material to an already dried polymeric material layer.

Once the initial layer or layers of polymeric solution are deposited on the cylindrical mandrel a spring material, preferably a stainless steel spring or a shape memory alloy spring, is applied to the cylindrical mandrel. In one embodiment, the spring may be in an uncoiled configuration, either flat or round in size, and wound around the polymer-coated mandrel by known mechanical means. Alternatively, the spring may be provided in a pre-coiled configuration and inserted over the mandrel. In further embodiments, the spring material may be wound around the mandrel or inserted thereover simultaneously with the application of the polymer solution.

The choice of the number of windings per inch for the spring or the diameter or cross-sectional area of the spring material may vary depending upon the desired spring properties and flexibility of the ultra-thin walled wire reinforced endotracheal tube. Furthermore, it should be understood that the spring material cross-sectional area, or diameter if the spring material is round, should be sized to provide the ultra-thin walled wire reinforced endotracheal tubing having a reduced wall thickness while maintaining sufficient strength to avoid kinking or bending during handling and subsequent constriction of an airway passage. According to one exemplary embodiment a flat 0.1×0.5 mm wide ribbon of work hardened stainless steel #304 spring wire at a pitch of 24/inch was wound on the polymer coated the mandrel.

In further embodiments of the invention, a shape memory alloy such as Nitinol is incorporated as the reinforcing wire. As discussed above, the properties of shape memory alloys allow fabrication of endotracheal tubes that are crush proof, i.e. following manual occlusion, recovery was complete.

Once the spring wire is applied to the mandrel, further deposition of polymeric material may be performed to yield a smooth outside surface having the desired final diameter. After application, the polymeric material is first air dried, and then the mandrel is contacted with circulating hot air for final cure. According to one preferred embodiment, the total wall thickness, including wire reinforcement, is approximately 0.2 mm.

Figure 5:
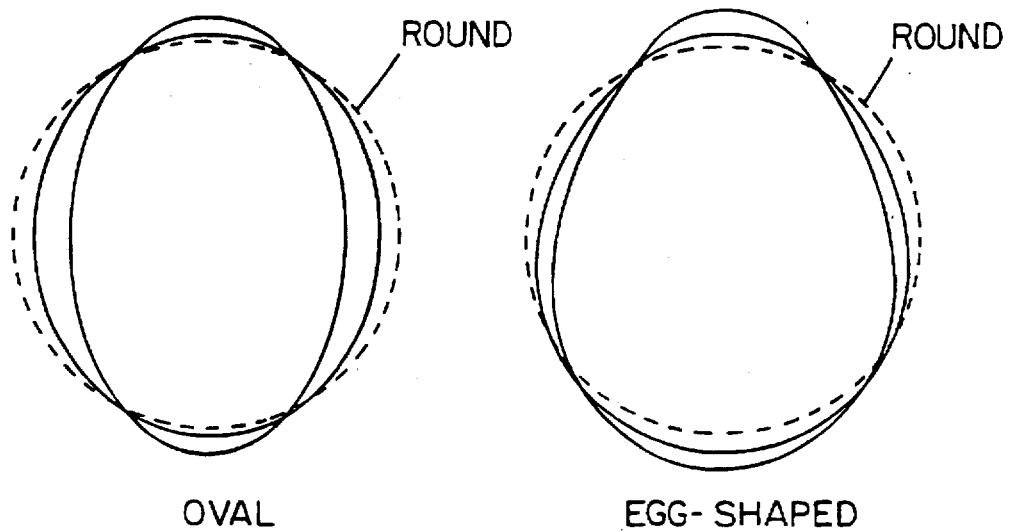
FIG. 5 is schematic cross sectional view of a laryngeal section of an endotracheal tube which depicts an oval shape.
Figure 4:
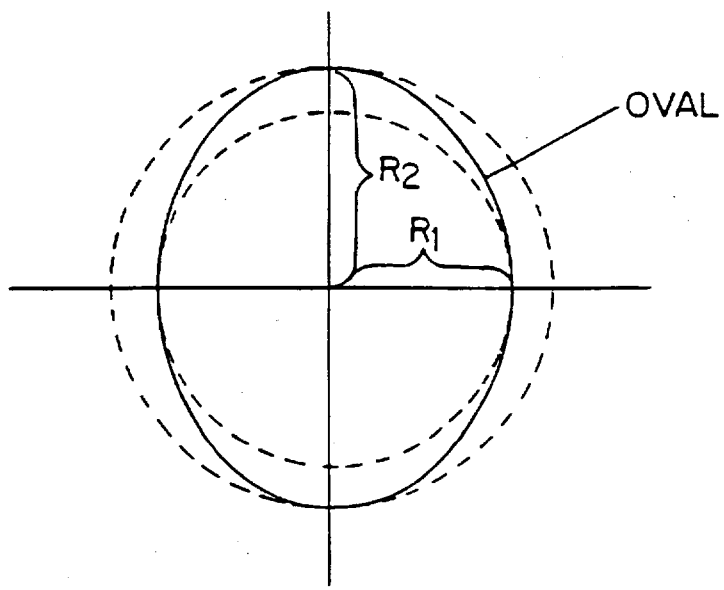
FIG. 4 is schematic cross sectional view of a laryngeal section of an endotracheal tube which depicts various changes in shape applicable to the present invention.

Following final cure, the body of the endotracheal tube is removed from the mandrel. Endotracheal tubes reinforced with non-shape memory alloy materials, e.g. stainless steel wire were then placed in a press which shaped a 4–5 cm section of the second stage of the ultra-thin two-stage endotracheal tube (which was to rest within the larynx) in such manner that it became oval (or egg shaped) in cross-sectional view as illustrated in FIG. 4. During this shaping process, the lesser axis $R_1$ is reduced in width to the approximate outside diameter of the first stage of the ultra-thin two-stage endotracheal tube, while the greater axis $R_2$ is proportionately increased as depicted in FIG. 5. It was the purpose of this design to shape the endotracheal tube to better conform to the approximate anatomical dimensions of the airway at the level of the vocal processes and the larynx, rather than to adhere to the traditional round endotracheal tube design, i.e. to shape the endotracheal tube so that it would better match the longer antero-posterior dimension of the glottic opening, and be narrower in the transverse width. Following trimming and finishing operations, the endotracheal tubes containing the shape memory alloy springs were heat set to a desired curved configuration. It is pointed out that while oval or egg-shaped laryngeal sections were provided according to a preferred embodiment, other non-circular shapes including triangular, pentagonal, and other polygonal shapes can be used since these shapes are more similar to the cross section of a larynx than a circular shape.

When a shape memory alloy spring is used, it is necessary to form the shape memory alloy into a desired configuration and then heat or apply electrical stimulation to the shape memory alloy in order to "set" the shape memory alloy in the desired shape. Thereafter, once deformed, the shape memory alloy will return to the desired configuration. Such means of forming shape memory alloys is known and can be applied before the shape memory alloy material is applied on the mandrel. Any suitable shape memory alloy can be used according to the present invention, including, for example Ti—Ni alloys (including Nitinol) and Cu—Zn—Al alloys.

After the polymer has been applied and cured, the sealing means described below are positioned on the formed polymer tubing either before or after the tubing is removed from the mandrel. The sealing means are fixed to the tubing by means of a suitable, biocompatible cement, selected from those known in the art. According to another embodiment, the sealing means may be positioned on the tubular member prior to complete curing of the polymer. Thereafter, the curing of the polymer may be used to secure the sealing means. Other suitable means such as welding or heat sealing the sealing means on the tubular member could also be used.

The seal means for the endotracheal tube can be vacuum molded from 0.025 or 0.075 mm thick soft, pliable polyurethane sheets to provide a series of doughnut shaped discs (referred herein as "gills" or "flanges"), which are solvent cemented onto the endotracheal tube. When the endotracheal tube is provided with a non-circular laryngeal section, the seal elements are attached to this portion of the endotracheal tube. (There are no "gills" placed on the tracheal portion of the endotracheal tube.) The external diameter of those "gills" should be about 50–100% larger than the outside diameter of the endotracheal tube. The purpose of the "gills" is to provide in effect a "no pressure" seal at the level of the larynx, to help reduce/eliminate possible air leaks from around the endotracheal tube.

With reference to FIGS. 6A and 6B, a comparison is illustrated between prior art endotracheal tubes and the ultra-thin walled wire reinforced endotracheal tubing of the present invention. As can be seen from FIG. 6A, the prior art endotracheal tube having an outer diameter of 10.7 millimeters has an inner diameter of 7.5 millimeters due to the wall thickness of 1.6 millimeters. In contrast, the ultra-thin wall wire reinforced endotracheal tubing of the present invention may be made having the same outer diameter of 10.7 millimeters but with an increased inner diameter of 10.2 millimeters as a result of the reduced wall thickness of 0.2 millimeters.

Referring to FIGS. 7A and 7B, a similar comparison is made wherein the prior art endotracheal tubing 33 is compared to the ultra-thin walled wire reinforced endotracheal tubing 35 of the present invention. In this manner, the prior art endotracheal tubing 33 having an outer diameter of 9.3 millimeters has an inner diameter of 6.5 millimeters. The ultra-thin walled wire reinforced endotracheal tubing 35 has an increase in the inner diameter to 8.8 millimeters for the same 9.3 millimeter outside diameter.

Figure 8:
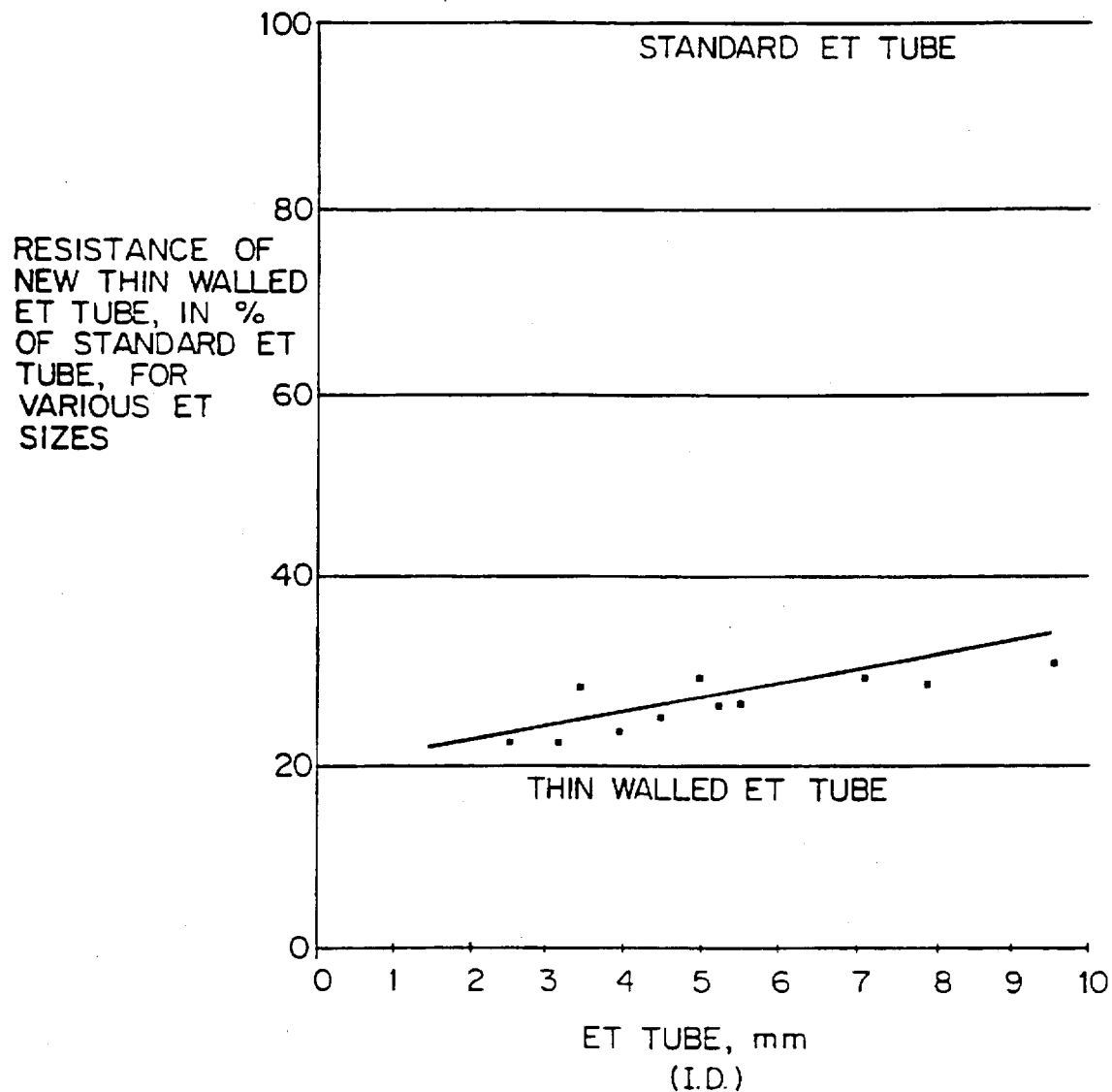
FIG. 8 shows a graph comparing air resistance in the inventive ultra-thin walled endotracheal tube as compared to prior art endotracheal tubes.

With reference now to FIG. 8, a graph is depicted which compares standard endotracheal tubes such as those depicted in FIGS. 6A and 7A with the ultra-thin walled wire reinforced tubing of the present invention having a wall thickness of approximately 0.2 millimeters. The graph compares the resistance of the inventive thin walled endotracheal tubing as a percent of the air resistance of the standard endotracheal tubing for a range of endotracheal tubing based upon inner diameters. As can be seen from the graph in FIG. 8, the inventive thin walled endotracheal tubing results in a substantial decrease in resistance as compared to prior art endotracheal tubing. In addition, air flow resistance is further lowered for smaller sized endotracheal tubes which provides reduced air resistance in endotracheal tubing adapted for newborn patients.

Figure 9:
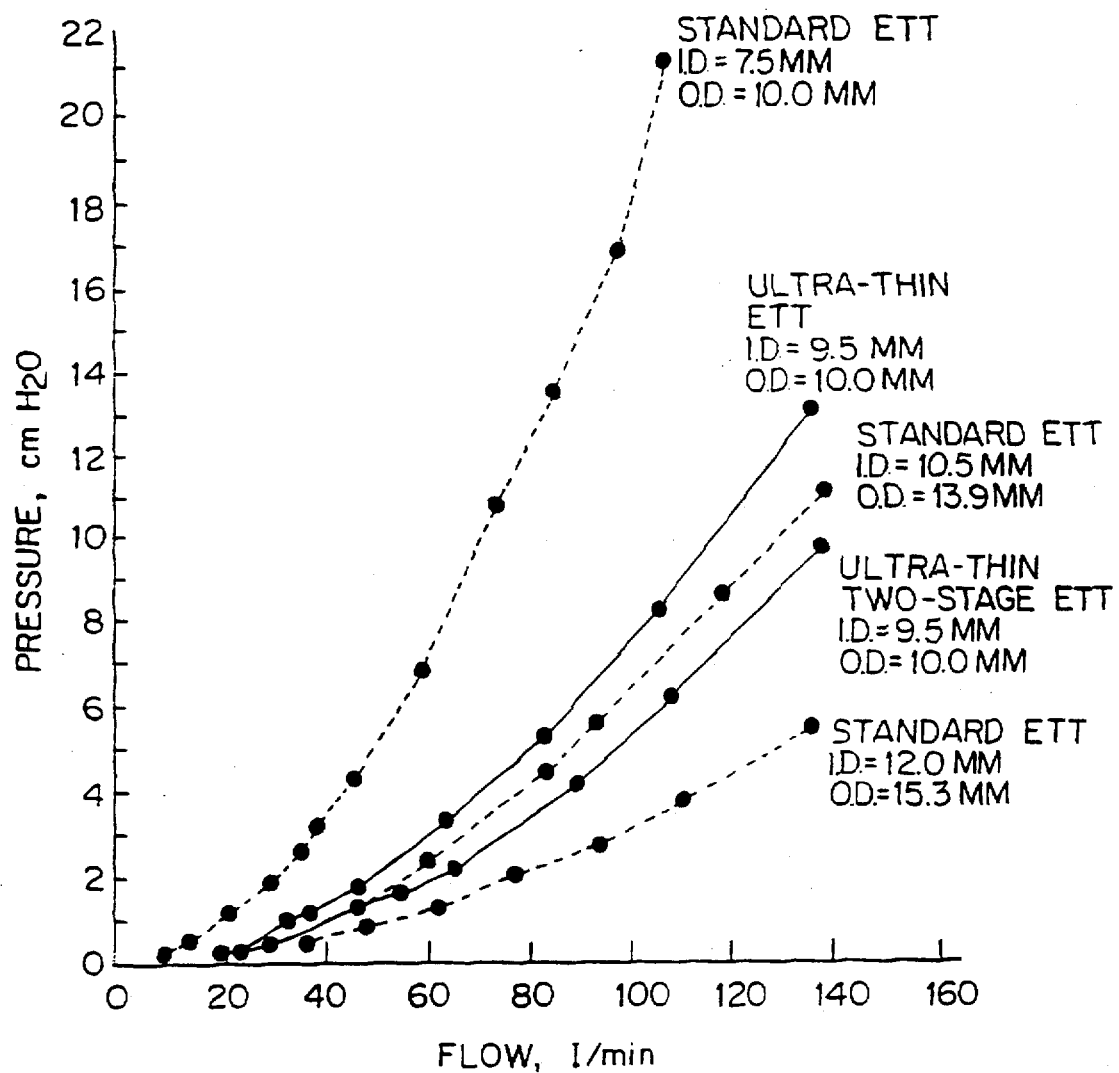
FIG. 9 shows a graph comparing pressure/flow studies of various endotracheal tube designs.

In vitro pressure/flow studies were performed using various sizes of the endotracheal tubes of the present invention. Pressure/flow studies were also performed on standard, commercially available endotracheal tubes from various manufacturers (Sheridan, Mallinkrodt) The results of these in vitro studies are depicted in FIG. 9. From pressure/flow curves it became possible to compute static air flow resistance for all endotracheal tubes, at given air flow. As the pressure flow curves of commercially available endotracheal tubes did not differ much from manufacturer to manufacturer, they were listed as "standard endotracheal tubes". Because of great difference in wall thickness between standard endotracheal tubes and the endotracheal tubes of the present invention, it was pointless to equate the present endotracheal tubes by the internal diameters. Rather, we chose to equate the present endotracheal tubes with the same, or a hypothetical standard endotracheal tube (the "equivalent standard endotracheal tube") that had the same pressure-flow characteristics. See Table 1 below.

Figure 10:
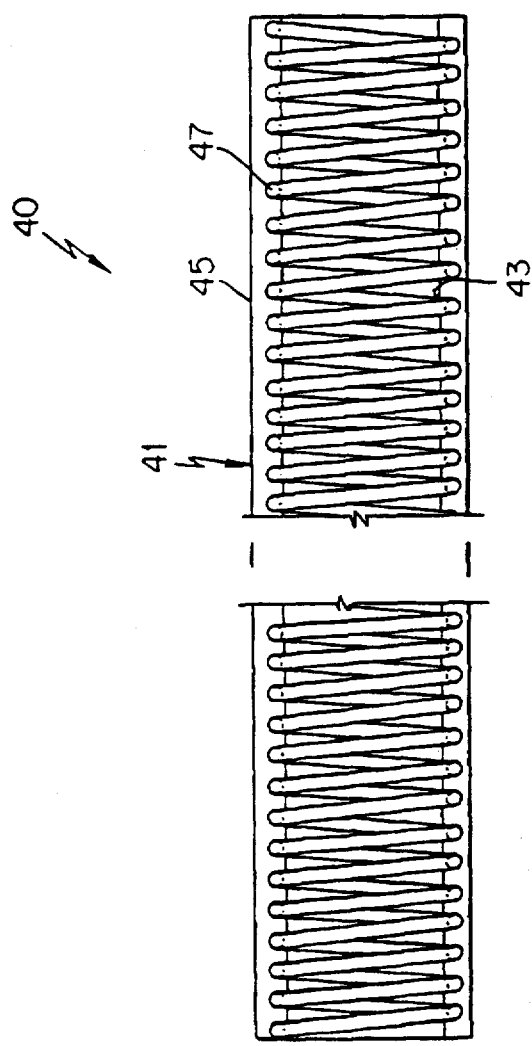
FIG. 10 shows an exemplary ultra-thin walled wire reinforced endotracheal tube showing the spring material incorporated in the endotracheal tubing wall.

With reference now to FIG. 10, an exemplary ultra-thin walled wire reinforced endotracheal tubing is generally designated by the reference numeral 40. The thin walled wire reinforced endotracheal tubing includes a tubing wall 41 having an inner surface 43 and outer surface 45. Incorporated within the tubing wall 41 is a spring 47. The diameter of the spring material 47 is sized in conjunction with the applied layers of polymeric material to provide the minimum wall thickness while maintaining sufficient strength to permit handling of the endotracheal tube. As disclosed above, a wall thickness of about 0.2 millimeters is attainable using the inventive method and apparatus for making the ultra-thin walled wire reinforced endotracheal tubing. The wall thickness of about 0.2 mm is a preferred thickness with the wall thickness ranging between about 0.1 mm and 0.5 mm. A preferred range for the wall thickness includes between about 0.15 mm and 0.35 mm. For a given wall thickness of 0.2 millimeters, it should be understood that the diameter of the wire spring material is less than the wall thickness to provide a polymeric layer along the inner and outer surfaces, 43 and 45 respectively of the tube 40. Alternatively, the wire spring material when positioned on the cylindrical mandrel prior to deposition of polymeric material may form part of the inner surface 43 of the tubing 40.

FIG. 11 is a schematic cross sectional side view of an ultra-thin two-stage endotracheal tube according to the present invention. As depicted in FIG. 11, the ultra-thin two-stage endotracheal tube includes a first stage portion (stage 1) which has a diameter compatible to a subject's trachea and a second stage portion (stage 2) which has a diameter compatible to a subject's oropharyngeal structure. The first and second stage portions are connected together by a tapered portion which is tapered at about 2°.

The apparatus and method of making the ultra-thin walled wire reinforced endotracheal tubing provides a endotracheal tube having a thin wall thickness not attainable in prior art endotracheal tube making apparatus or methods. The inventive apparatus and method also provide flexibility in adapting the manufacture of the inventive endotracheal tubing for various configurations for operating conditions such as an eccentric or slightly out of round mandrel. By having the nozzle of the metering pump 9 float or follow the contour of the mandrel, any slight out of roundness and/or eccentricity of the mandrel can be easily accommodated without effecting the quality of the tube.

In addition, the method of applying the polymer solution along the length of the mandrel permits programming of the control means to achieve different tubing configuration. For example, by increasing the flow rate of the dissolved polymer or reducing the rotation of the mandrel in conjunction with controlling the travel of the nozzle 11 along the mandrel, varying thicknesses of wall tubing may be obtained. By programming of more layers of different thicknesses on different parts of the mandrel, utilizing the control means, tapered endotracheal tubes may be manufactured. Alternatively, the mandrel 1 may be made having a tapered configuration wherein a tapered spring material may be used in conjunction with a uniform coating to produce a tapered tube having a uniform wall thickness.

Figures 12A, 12B:
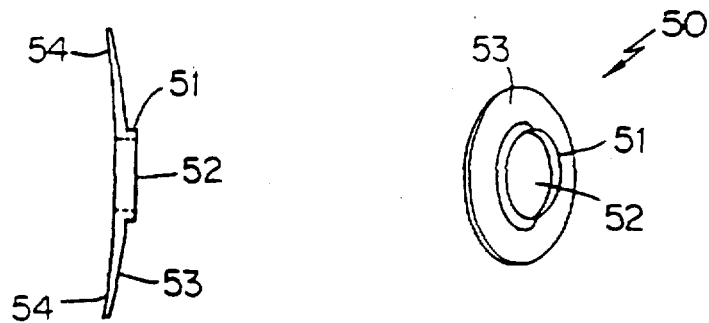
FIG. 12A is a perspective view of a sealing means according to one embodiment of the present invention.
FIG. 12B is a cross sectional view of the sealing means of FIG. 12A.
Figure 13A:
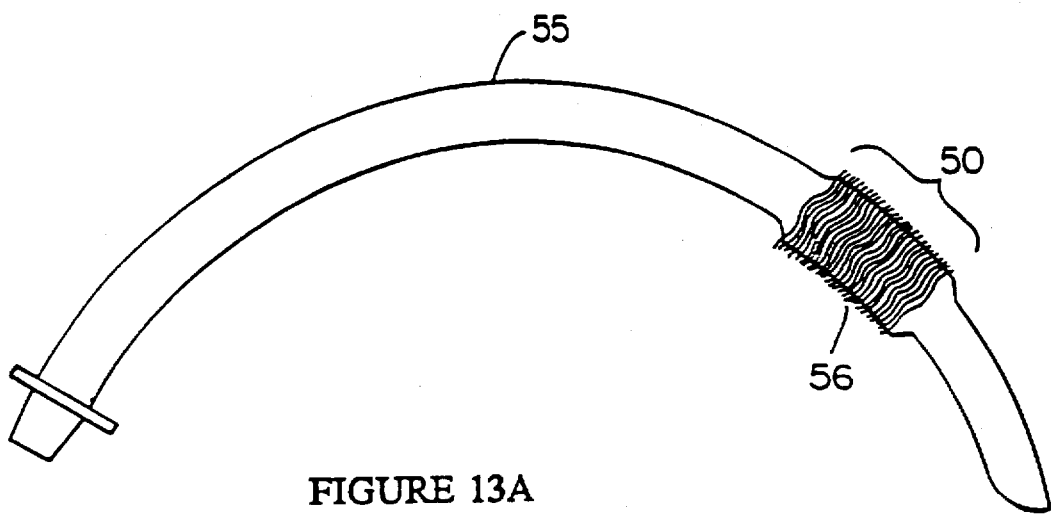
FIG. 13 shows an endotracheal tube according to one embodiment of the present invention which includes the sealing means of FIG. 12A.
Figure 13B:
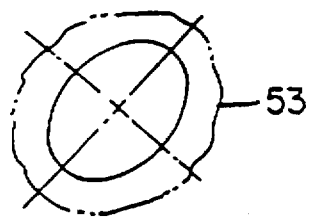

FIG. 12A shows a sealing means 50 according to one embodiment of the present invention. As shown, the sealing means 50 is a gilled- or flanged-collar. The collar portion 51 includes a through-bore 52 which allows a tubular member to be inserted within the sealing means 50 and fixed thereto as shown in FIG. 13. The gill or flange 53 of the sealing means 50 is a thin, soft, pliable element made of a suitable biocompatible plastic material such as polyvinyl chloride, silicone rubber, polyethylene or the like, and is preferably integral with the collar portion 51, which may be made of a similar plastic material.

In a preferred embodiment, the gill or flange 53 of the sealing means 50 is made of a thin, e.g., 0.05 mm polyurethane, vacuum formed, and then cut and punched to an appropriate size. Other suitable methods of fabricating the sealing members, such as injection molding, separately fabricating and attaching the collar and flange portions, etc. could also be utilized. The thickness of the gill or flange portion should be relatively thin to ensure that the gill or flange is suitable soft and pliable. According to one embodiment of the present invention, the gills or flanges were as thin as about 0.01 mm. In another embodiment the gills or flanges were between about 0.025–0.05 mm thick. While the thickness of the gills or flanges can be greater than 0.05 mm, depending on the pliability of the material from which they are formed, the limiting factor on this thickness is the ability of the gills or flange portions to provide the desired seal discussed above.

FIG. 12B show a cross section of the seal means of FIG. 12A. As shown, the gill or flange 53 extends from collar portion 51. The cross sectional area of the gill or flange 53 is tapered as illustrated so as to be thicker near the collar 51. The free edge 54 of the gill or flange 53 is feathered as shown. The gill or flange 53 may extend perpendicular from the collar 51 either straight or with a slight curve. The curved shape of the gill or flange 53 which is illustrated in FIG. 12B may provide a better seal when a tubular member having curved gills or flanges 53 is first inserted then backed out a short distance to reverse the curve of the gills or flanges 53 from the direction in which they are oriented when being inserted. In this embodiment, the curve shape can provide a small bias force to the seal means.

For an endotracheal tube, the diameter of the gills or flange portions can range from as small as 0.5 mm to 1 cm or more. The diameter or the gills or flanges can be determined from the outside diameter of the tubular member and the inner diameter of the lumen and should generally be about 50–100% larger than the outside diameter of the endotracheal tube.

According to one design, the diameter of the gills or flanges as measured from the collar to the free end is between about 0.5–5.0 mm. The thickness of the gills or flanges at the collar is about 0.06mm and the feathered edge is about 0.02mm thick. Equally well, they could be of even thickness throughout.

FIG. 13 shows an endotracheal tube 55 having the sealing means 50 of FIG. 12A attached thereto. As shown, the sealing means 50 are located at a laryngeal section 56 of the endotracheal tube 55 which has a non-circular cross section. In FIG. 13, twenty-two sealing members are shown on the endotracheal tube 55. However, it is noted that any number of sealing means including one, ten, twenty, thirty or more could be utilized.

Figure 14:
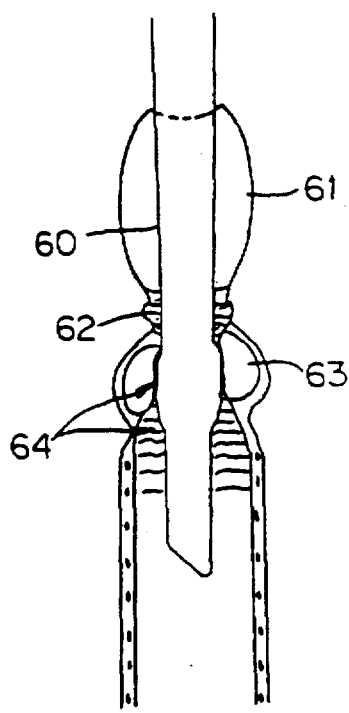
FIG. 14 shows an endotracheal tube with a sealing means according to the present invention positioned in a larynx-trachea.

FIG. 14 shows an endotracheal tube according to the present invention which is positioned in a larynx-trachea. As shown in FIG. 14 the endotracheal tube 60 is inserted through the epiglottis 61, vocal cord area 62 and the cricoid 63. The gills or flanges 64 of the sealing means (collars are not shown) which are located within the narrow or constricted portion of the lumen adjust to the inner diameter of this portion of the lumen due to their pliability and form a seal between the endotracheal tube 60 and the inner wall of the lumen.

It has been found that the gills or flanges will accommodate the anatomy of the trachea and that some tracheal bronchial secretions are likely to be entrapped between the gills or flanges, thus assisting sealing off air/oxygen leakage. More importantly, there is almost negligible pressure on the adjacent epithelium of the trachea. This greatly reduces or eliminates tracheal wall injury. It is further noted that the tapering of the gills or flanges as discussed above helps protect the tracheal epithelium from possible undue physical trauma.

As can be understood from FIG. 14, the diameter of the gills or flanges 64 of the sealing means should be substantially larger than the distance between the outer wall of the tubular member 60 and the inner wall of the lumen.

The sealing means of the present invention have a particular advantage in that they can be utilized in conjunction with endotracheal tubes which are less than about 5mm in diameter. Heretofore, no sealing means, e.g. inflatable cuffs, was provided for such small endotracheal tubes. Of course, in addition to being particularly useful for small (less than about 5 mm) diameter endotracheal tubes, the sealing means of the present invention could also be suitable sized and utilized with larger diameter tubes.

The sealing means of the present invention has been found to be especially useful in conjunction with the above-discussed ultra-thin wall walled wire reinforced endotracheal tubes. This combination provides endotracheal tubes which have low airway resistance and a maximum inside diameter for a given outside diameter. By utilizing the sealing means of the present invention in stead of inflatable cuffs on these ultra-thin walled endotracheal tubes, possible deformation of the tubes caused by inflating or over inflating of the cuffs can be avoided. Moreover, as in the case of any type of endotracheal tube, use of the sealing means of the present invention in place of inflatable cuffs avoids the need for additional fluid passages needed to inflate and deflate the cuffs, thus allowing reduction of the overall diameter of the tubes.

The following example is presented to illustrate features and characteristics of the present invention which is not to be considered as limited thereto.

EXAMPLE

After premedication with pentobarbital, the trachea of 26–28 kg sheep were incubated with a commonly available hollow introducer, over which an ultra-thin two-stage endotracheal tube of the present invention was readily glided into place. The location and position of the oval (egg shaped) portion of the endotracheal tube was carefully verified by direct vision, and by roentgenographic films. The endotracheal tube was then secured to a bite block. The sheep were maintained under general anesthesia using phenobarbital at 4 mg/kg h, and pancuronium bromide at 0.06 mg/kg h. The sheep were placed on a Siemens 900 C Servo Ventilator, and were ventilated at a respiratory rate of 15/min, and an initial tidal volume (VT) of 8–10 ml/kg in the volume controlled mode. To achieve a higher peak inspiratory pressure (PIP), VT was increased so as to raise PIP in increments of 5 cm change $H_2O$, up to 50 cm $H_2O$. PEEP was thereafter raised to 5 and 10 cm $H_2O$, and the experiment was repeated.

Air leak was computed from difference in inspiratory and expiratory tidal volumes, as read off the Servo Ventilator. Similar studies were also performed with a standard endotracheal tube of approximately same outside diameter, in which the cuff had been excised, or not inflated. The purpose of those studies was to assess air leak around a standard endotracheal tube of approximately same outside diameter at the level of the larynx, i.e. at the narrowest portion of the upper airways, and without relying upon the inflated cuff of the standard endotracheal tube for an airway seal.

In two separate studies, controlled ventilation in healthy anesthetized sheep, intubated with ultra-thin two-stage endotracheal tube of appropriate dimensions for the size of the sheep was conducted for 24 hours. After ventilation, the sheep were electively sacrificed. The trachea was carefully dissected, the changes in the trachea and the larynx were carefully noted.

The endotracheal tubes were found to be highly flexible, they could be acutely bent without kinking, and transmitted little torque on manual twisting. The endotracheal tubes of the present invention weighed approximately one third the weight of conventional PVC endotracheal tubes. Upon pressurization, there was some distension in the longitudinal direction, but not radially, i.e. while the tubes would lengthen, its diameter did not change. This lengthening was a function of wall thickness, and ranged from 0.05 mm/cm $H_2O$ pressure for a 30 cm long endotracheal tube, with a wall thickness of 0.2 mm, to substantially less in endotracheal tubes with heavier walls.

While endotracheal tubes produced with stainless steel wire required moderate care to avoid damage, the endotracheal tubes reinforced with a shape memory alloy, e.g. Nitinol wire were uniquely different, as they could be occluded by forceful finger pressure, for example, with full and complete recovery upon release of pressure.

The increase in internal diameter in the new line of ultra-thin endotracheal tube was achieved solely on the basis of decrease in wall thickness, as seen in Table 1.

TABLE 1

CROSS-SECTIONAL DIMENSIONS OF STANDARD, ULTRA-THIN AND ULTRA-THIN TWO-STAGE ENDOTRACHEAL TUBES OF SAME LENGTH

| Standard ETT | | UT ETT | | UTTS ETT | | | | Equivalent to |
| --- | --- | --- | --- | --- | --- | --- | --- | --- |
| | | | | 1st stage | | 2nd stage | | |
| ID mm | OD mm | ID mm | OD mm | ID mm | OD mm | ID mm | OD mm | standard ETT mm I.D. |
| 2.5 | (3.6) | 3.2 | (3.6) | 3.2 | (3.6) | 5.0 | (5.4) | 4.2 |
| 2.8 | (4.0) | 3.6 | (4.0) | 3.6 | (4.0) | 5.0 | (5.4) | 4.7 |
| 3.6 | (5.1) | 4.6 | (5.1) | 4.6 | (5.1) | 5.8 | (6.2) | 5.5 |
| 3.8 | (5.4) | 4.9 | (5.4) | 4.9 | (5.4) | 6.4 | (6.8) | 5.7 |
| 5.2 | (6.8) | 6.35 | (6.6) | 6.35 | (6.8) | 7.9 | (8.3) | 7.6 |
| 5.7* | (7.6) | 7.2 | (7.6) | 7.2 | (7.6) | 9.2 | 9.7 | 8.0 |
| 6.2* | (8.3) | 7.9 | (8.3) | 7.9 | (8.3) | 9.5 | 10.0 | 9.0 |
| 7.5 | (10.0) | 9.5 | (10.0) | 9.5 | (10.0) | 11.0 | 11.4 | 10.8 |
| 8.0 | (10.7) | 10.3 | (10.7) | 10.3 | (10.7) | 12.5 | 12.9 | 11.7 |

*Dimension of imputed standard ET tube, with standard wall thickness.
Note:
In the ultra-thin two-stage endotracheal tube (UTTS ETT), the first stage was limited to 6 cm, with the remainder made up of the larger second stage By virtue of a smaller wall thickness, the internal diameter of a 7.5 mm conventional size endotracheal tube was increased to 9.5 mm in the ultra-thin endotracheal tube, the outside diameter being the same (10.0 mm) (Table 1). At a gas flows between 0.5 and 1 1/sec, this amounted to a 2–3 fold decrease in air flow resistance (FIG. 9). In the two stage ultra-thin two-stage endotracheal tube, with the outside diameter of the tracheal portion of the ultra-thin two-stage endotracheal tube same as that of a standard 7.5 mm endotracheal tube, the pressure flow curve was equal to an imputed 10.8 mm standard endotracheal tube (Table 1, FIG.

8); at a gas flow from 0.5 to 1 1/sec, this amounted to a 4-5 fold decrease in air flow resistance.

When the ultra-thin two-stage endotracheal tube, with oval cross-section (lesser axis, outside diameter equivalent to a 8.7 mm conventional endotracheal tube; greater axis, outside diameter equivalent to a 10.5 mm conventional endotracheal tube) (FIG. 5), and attached "gills" at the level of the larynx was set in the proper position, there was no air leak at pressures up to 30 cm $H_2O$, at PEEP to 10 cm $H_2O$, in a 28 kg sheep; there was a minimum air leak starting at pressures 30-35 cm $H_2O$, as seen in Table 2.

TABLE 2

| Peak airway pressure, cm $H_2O$ | UTTS ETT | | Standard Round ETT, | | |
|---|---|---|---|---|---|
| | Horizontal axis I.D. 11.4 mm O.D. 11.9 mm | Vertical axis I.D. 14.2 mm O.D. 14.7 mm | without cuff I.D. 9.0 mm O.D. 12.0 mm | | |
| | PEEP cm $H_2O$ | | PEEP, cm $H_2O$ | | |
| | 0 | 5 | 10 | 0 | 5 | 10 |
| 15 | 0 | 0 | 0 | 80% | >90% | 100% |
| 20 | 0 | 0 | 0 | 82% | >90% | 100% |
| 25 | 0 | 0 | 0 | 82% | >90% | 100% |
| 30 | 0 | 6 | 0 | | | |
| 35 | 5 | 6 | 4 | | | |
| 40 | 10 | 12 | 8 | | | |
| 45 | 19 | 11 | 8 | | | |

In contrast, there was a prohibitive air leak over 80% at any PEEP level when using a conventional 9.0 mm endotracheal tube (outside diameter 12.0 mm), with the cuff removed, or not inflated. Following 24 hours of mechanical pulmonary ventilation with same ultra-thin two-stage endotracheal tube, there was no significant change in air leak from start of the studies.

Upon sacrifice, the trachea looked unremarkable, and healthy. The ultra-thin two-stage endotracheal tube was loosely positioned, the vocal cords looked unremarkable; a small pressure point could be seen in the glottis.

Although the present invention has been described with reference to particular means, materials and embodiments, from the foregoing description, one skilled in the art can ascertain the essential characteristics of the present invention and various changes and modification may be made to adapt the various uses and characteristics thereof without departing from the spirit and scope of the present invention as described in the claims which follow.

What is claimed is:

1. A passive continuous positive airway intratracheal pulmonary ventilation apparatus which comprises:

an inspiration limb having an inspiration passageway with a one way valve therein:

an expiration limb having an expiration passageway with a one way valve therein and an exhaust port;

a connector joining an end of each of the inspiration passageway and the expiration passageway so that the inspiration passageway and expiration passageway are in communication with each other;

an endotracheal tube, one end in communication with both the expiration passageway and the inspiration passageway via the connector; and means for generating a constant positive pressure in each of the inspiration limb and the expiration limb and for maintaining the constant positive pressure at a near equal level in each of the inspiration limb and the expiration limb, the positive pressure generating and maintaining means further comprising a first inflatable bag in communication with the inspiration passageway, a second inflatable bag in communication with the expiration passageway, a throttle valve as said exhaust port to provide a constant expiratory leak during inspiration and expiration and a means for applying a constant force to each of the first and second inflatable bags;

whereby a oxygen containing gas is supplied to a patient via the inspiration passageway and endotracheal tube and expiration flow from said patient is supplied to said expiration passageway via the endotracheal tube and wherein maintaining of the constant positive pressure to a nearly equal level permits a patient to both inhale and exhale at peak inspiratory and expiratory flow rates without a resistance which would cause patient exhaustion or shortness of breath.

2. A passive continuous positive airway intratracheal pulmonary ventilation apparatus according to claim 1, further comprising a intratracheal pulmonary ventilation system which includes a catheter, said catheter having a tip which extends through said endotracheal tube and an end opposite the tip which is connected to a continuous flow on an oxygen-containing gas.

3. A passive continuous positive airway intratracheal pulmonary ventilation apparatus according to claim 2, wherein said catheter tip includes means for directing the continuous flow of the oxygen-containing gas in a reverse direction.

4. A passive continuous positive airway intratracheal pulmonary ventilation apparatus according to claim 2, wherein, said intratracheal pulmonary ventilation system is connected to the connector.

5. A passive continuous positive airway intratracheal pulmonary ventilation apparatus according to claim 2, wherein said intratracheal pulmonary ventilation system further includes a pressure monitoring catheter which passes through said endotracheal tube.

6. A passive continuous positive airway intratracheal pulmonary ventilation apparatus according to claim 1, wherein each of said means for applying a constant to said first and second inflatable bags comprises a weight.

7. A passive continuous positive airway intratracheal pulmonary ventilation apparatus according to claim 6, wherein said means for applying a force to said first and second inflatable bags comprise means for supporting said weights above said first and second inflatable bags.

8. A passive continuous positive airway intratracheal pulmonary ventilation apparatus according to claim 7, wherein said means for supporting said weights comprise a hinged frame assembly.

9. A passive continuous positive airway intratracheal pulmonary ventilation apparatus according to claim 1 wherein said endotracheal tube comprises a wire-reinforced endotracheal tube.

10. A passive continuous positive airway intratracheal pulmonary ventilation apparatus according to claim 9, wherein said wire-reinforced endotracheal tube has a uniform wall thickness of between about 0.15 mm and 0.35 mm.

11. A passive continuous positive airway intratracheal pulmonary ventilation apparatus according to claim 9, wherein said wire-reinforced endotracheal tube is reinforced with a shape memory alloy material.

12. A passive continuous positive airway intratracheal pulmonary ventilation apparatus according to claim 1, wherein said endotracheal tube includes a plurality of sealing means are provided on an exterior surface thereof.

13. A passive continuous positive airway intratracheal pulmonary ventilation apparatus according to claim 12, wherein said plurality of sealing means have a thickness of about 0.02 to 0.075 mm.

14. A passive continuous positive airway intratracheal pulmonary ventilation apparatus according to claim 1, wherein said endotracheal tube comprises:

a first generally cylindrical portion having a first diameter;

a second generally cylindrical portion having a second diameter, said second diameter being greater than said first diameter; and a tapered portion connecting said first and second generally cylindrical portions.

* * * * *